United States Patent [19]

McPhaul

[11] 4,443,941
[45] Apr. 24, 1984

[54] INTRAMEDULLARY PIN CUTTING INSTRUMENT

[76] Inventor: Jack L. McPhaul, 17411 F.M. 529, Houston, Tex. 77095

[21] Appl. No.: 312,182

[22] Filed: Oct. 16, 1981

[51] Int. Cl.³ ............................................. B26D 1/09
[52] U.S. Cl. ........................................ 30/241; 30/92; 30/182; 128/318
[58] Field of Search .......................... 30/180, 182–185, 30/228, 241–243, 92; 128/92 E, 318; 269/32

[56] References Cited

U.S. PATENT DOCUMENTS

| | | | |
|---|---|---|---|
| 1,491,022 | 4/1924 | Arbon | 30/92 X |
| 2,558,641 | 6/1951 | Beezley | 30/182 X |
| 2,755,550 | 7/1956 | Benjamine | 30/180 |
| 2,863,214 | 12/1958 | Szappanyos | 30/241 X |
| 3,093,024 | 6/1963 | Pell | 30/182 X |
| 3,906,628 | 9/1975 | Hastings | 30/182 |

FOREIGN PATENT DOCUMENTS

| | | | |
|---|---|---|---|
| 503563 | 6/1920 | France | 30/182 |
| 1375794 | 9/1964 | France | 30/182 |

Primary Examiner—E. R. Kazenske
Assistant Examiner—Douglas D. Watts
Attorney, Agent, or Firm—Hubbard, Thurman, Turner, Tucker

[57] ABSTRACT

An instrument for cutting elongated pins used in orthopedic surgery includes a housing having a reduced diameter portion in which is disposed a piston reciprocable in a fluid chamber. An enlarged diameter portion of the housing forms a further part of the fluid chamber in which is disposed a second piston connected to a member forming a first cutting edge which is movable toward an anvil having a second cutting edge cooperable with the first cutting edge to shear a pin to a predetermined length. The smaller piston is engaged by a screw actuator disposed on the housing and which may be rotated to provide a substantial force multiplication whereby a sufficient cutting force is exerted on a pin. The instrument is provided with a transverse handle portion to facilitate handling and to hold the instrument against reaction forces of the screw actuator. The cutting edges are formed on cooperable anvil and actuating member portions. A reduced diameter nose portion of the instrument includes a transverse bore for supporting a pin to be cut.

7 Claims, 2 Drawing Figures

INTRAMEDULLARY PIN CUTTING INSTRUMENT

BACKGROUND OF THE INVENTION

1. Field of the Invention

The present invention pertains to an instrument for cutting elongated steel pins or rods insertable in the medullary cavity in repairing human and animal bone fractures. The instrument includes mechanical screw and hydraulic force multiplying mechanism for severing pins to a predetermined length prior to or after the pins have been inserted in the bone.

2. Background Art

In the performance of orthopedic surgery in both human and veterinary medicine, it is known to provide for repairing fractured bones by inserting steel pins of various cross-sectional shapes in the medullary cavity of the bone to support the bone sections on opposte sides of the fracture. Since the repair of some bone fractures requires the insertion of intramedullary support pins of varying lengths, it may be necessary to cut the pin during the surgical procedure once the required length of the pin has been determined. Quite often in the performance of a surgical procedure, a pin of more than sufficient length is inserted into the medullary cavity and then cut to the desired length prior to completion of the procedure.

Since intramedullary pins and the like are preferably formed of stainless steel, the procedure for cutting the pin after it has been inserted in the bone becomes difficult due to the strength and hardness of the pin material. Heretofore, various tools such as saws and pivoting jaw type cutters have been used to cut intramedullary pins to the required length both before and during the surgical procedure. The use of these devices has been generally unsatisfactory in that they are cumbersome and difficult to manipulate properly. Known techniques for cutting intramedullary pins, particularly when they have already been inserted into the bone, are generally unsatisfactory since it is usually required that the bone and associated portion of the patient's body be carefully maintained in a particular position without any forces exerted thereon during the procedure to avoid further damage to the fractured bone or other parts of the patient's body.

Accordingly, there has been a serious need for an instrument of a type particularly adapted for cutting intramedullary pins wherein the cutting operation may be performed before as well as after the pin has been inserted into the medullary cavity or the like. It is particularly desirable that the instrument be as compact and as easily handled as possible in the vicinity of the operating table by the person performing the surgery. It is also important that the instrument be applied to cut the pin without exerting any substantial forces on the portion of the pin already inserted into the bone so as to avoid further damage to the bone or other areas of the patient's body. Furthermore, the hardness of stainless steel intramedullary pins requires that an instrument be used which is capable of exerting substantial cutting forces without requiring an operating force greater than that which the average person using the instrument may easily exert.

It has been further determined that it is often desirable in the environment of a surgical operating room to provide instruments instruments which may be suitably manually actuated thereby eliminating the need for instruments requiring electrical or other sources of power which can be hazardous as well as inconvenient to use. These and other desiderata in the art of instruments for cutting intramedullary pins and similar members used in surgical procedures have been met by the apparatus of the present invention.

SUMMARY OF THE INVENTION

The present invention provides an improved instrument for cutting intramedullary pins and like elements used in surgical procedures, which instrument is adapted to provide a sufficient cutting force to shear relatively hard metal pins but which may be easily manually actuated without imposing unwanted forces on the pin after it has been already inserted into the medullary cavity.

In accordance with an important aspect of the present invention, there is provided a manually actuatable, hand held instrument which is capable of exerting very high cutting forces sufficient to cleanly shear stainless steel pins and the like with only nominal manual force being applied to the instrument by the operator. In accordance with another important aspect of the present invention, there is provided a compact hand held cutting instrument for intramedullary pins which may be manipulated with relative ease and which is operable to avoid unwanted reaction forces on the pin while it is being cut.

The pin cutting instrument of the present invention advantageously employs a combination of force transmitting mechanisms to provide a substantial cutting force required for intramedullary stainless steel pins, which mechanisms require only a moderate input force but are capable of providing a substantial mechanical advantage to develop a very high cutting force for shearing the pin between two cutting edges. In accordance with the present invention, an improved pin cutting instrument is provided which utilizes a mechanical screw for actuating a piston disposed within a chamber filled with hydraulic fluid, which chamber is in communication with a chamber of larger diameter and housing a piston connected directly to a member on which one of the cutting edges is disposed. Accordingly, a substantial mechanical advantage is derived through the screw actuator and due to the differential areas of the respective pistons so that a suitable shearing force is applied to the cutting edges with only a moderate turning force on the screw.

The present invention still further provides an improved pin cutting instrument which may be hand held and actuated to cut a pin already inserted into the medullary cavity without imposing any substantial lateral forces or twisting moment on the pin during the cutting operation. By providing an arrangement of an elongated screw actuator and a laterally extending support handle for the instrument housing, the reaction moment imposed on the instrument due to rotation of the actuating screw may be counteracted to substantially reduce any reaction forces imposed on the pin being cut.

The pin cutting instrument of the present invention still further provides an improved arrangement of elements providing a pair of opposed cutting edges which may be easily repaired or replaced, as required, if they should become dull or broken. Moreover, one of the cutting edges is formed on a member which may be easily adjusted to conform to the shear plane of the other cutting edge so that a uniform and complete cutting action is imposed on the pin.

Further superior features and advantages of the intramedullary pin cutting instrument of the present invention will be appreciated upon reading the detailed description which follows in conjunction with the drawings.

DESCRIPTION OF THE PREFERRED EMBODIMENT

Figure 1:
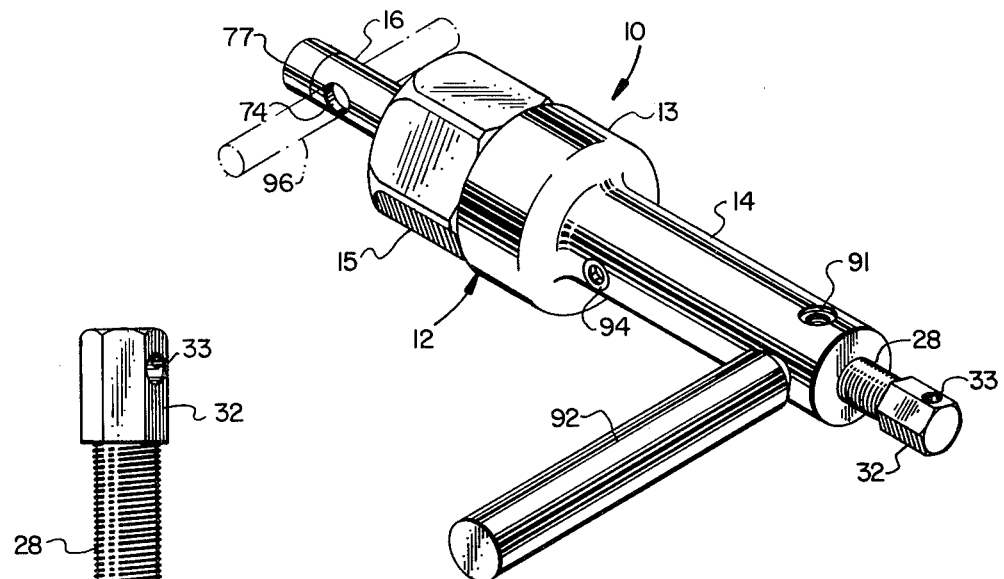
FIG. 1 is a perspective view of the intramedullary pin cutting instrument of the present invention.

Referring to the drawing figures, the pin cutting instrument of the present invention is illustrated and generally designated by the numeral 10. The instrument 10 includes a housing 12 comprising a first generally cylindrical section 13 having an elongated reduced diameter portion 14. The housing 12 includes a second section 15 which may have a cylindrical exterior shape or be formed in a hexagonal shape, as illustrated. The housing section 15 also includes a reduced diameter nose portion 16. The housing sections 13 and 15 are threadedly engaged with each other by respective internal and external threaded portions 17 and 18.

When the housing sections 13 and 15 are threadedly engaged they form a cylindrical chamber 19 for a purpose to be described in further detail herein. The distal end 20 of the cylindrical threaded portion 18 is engageable with a resilient gasket 21 disposed against a transverse wall 22 of the housing section 13. The chamber 19 is in direct communication with a further cylindrical chamber portion 23 formed by an elongated bore 25 within the reduced diameter portion 14 of the housing section 13. The bore 25 is closed at one end by a transverse wall portion 24 having an internally threaded bore 26.

The instrument 10 is provided with actuating mechanism including an elongated screw actuator 28 having threads complementary to the threads formed in the bore 26 whereby the screw actuator may be extended into the bore 25 for actuating a piston 30 slidably disposed within the bore 25 and delimiting the chamber 23. The portion of the screw actuator 28 extending out of the housing section 14 includes a hexagonal shaped head 32 which may be provided with a transverse bore 33 for receiving a turning handle or the like, not shown. Alternatively, the actuating screw 28 may be rotated by engaging the hexagonal head portion 32 with a wrench, also not shown.

The piston 30 is provided with suitable annular seals for engaging the bore 25 in sealing relationship thereto, which seals may comprise conventional o-rings 34, for example. A thrust bearing assembly is interposed between the face 38 of the piston and the end of the screw 28. The thrust bearing preferably includes spaced apart thrust washers 40 between which is disposed a bearing retainer 42 supporting a plurality of bearing balls or rollers. A distal end portion 44 of the screw 28 is provided with a somewhat spherical shape and projects into the interior of one of the races or washers 40 to help maintain the bearing centered against the piston face 38. By providing the thrust bearing 40, the screw actuator 28 may be rotated without requiring rotation of the piston 30 while also suitably reducing the friction forces between the end portion 44 and the piston.

The cutting instrument 10 includes a second piston 48 slidably disposed within a bore 50 formed within the housing section 15 and defining in part the chamber 19. The piston 48 is also provided with suitable seals for engaging the walls of the bore 50 comprising conventional o-rings 52. The piston 48 is removably connected to an elongated cylindrical member 54 disposed within a bore 56 formed in the nose portion 16 of the housing section 15. The member 54 is provided with a threaded portion 58 which extends into a complementary threaded hole 60 formed in the piston 48. The member 54 is further secured to the piston by a locknut 62. A helical coil type compression spring 64 is disposed around the member 54 and the locknut 62 and interposed between one face of the piston 48 and a transverse wall 66 formed within the housing section 15.

The end of the member 54 opposite the threaded portion 58 is provided with an axially projecting portion forming a cutting edge 68. The cutting edge 68 is cooperable with a complementary cutting edge 70 formed on an anvil member 72 to provide for shearing an element which may be interposed between the members 54 and 72 and within a transverse bore 74 formed in the housing portion 16. The anvil 72 comprises an externally threaded member which is engaged with an internal threaded portion 73 formed in the end of the housing portion 16. The anvil member 72 is secured in a desired position to be cooperable with the member 54 by a locknut 80. A removable cap 77 is threadedly engaged with the end of the housing portion 16 and covers the end of the anvil member 72 and the locknut 80 to minimize the chance of unwanted loosening of the nut and to provide a smooth exterior surface at the end of the housing portion.

Figure 2:
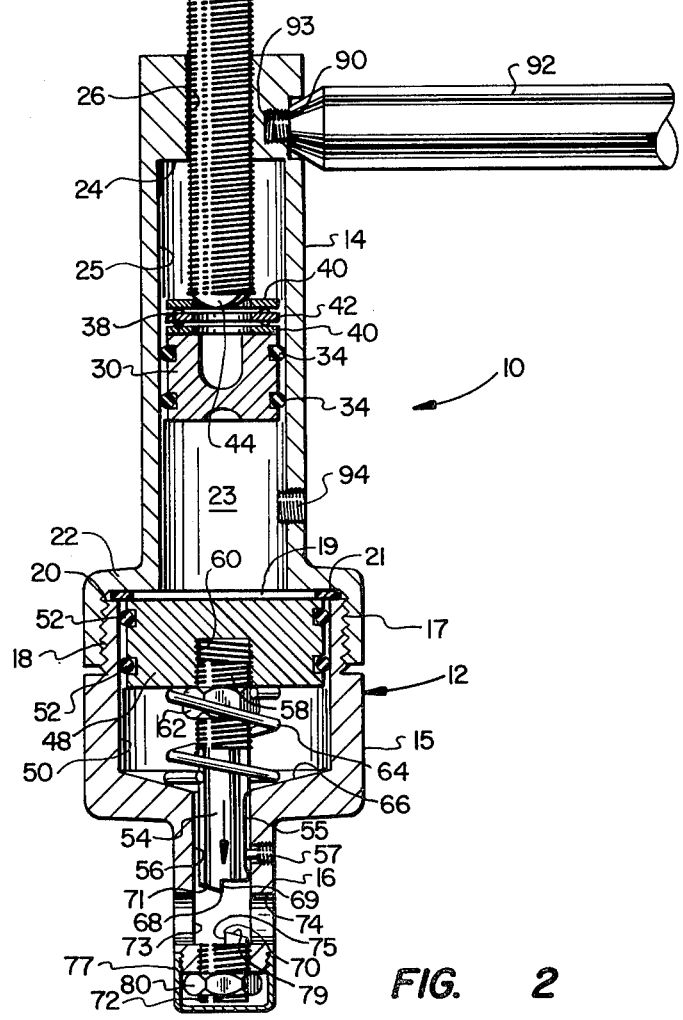
FIG. 2 is a longitudinal central section view of the pin cutting instrument illustrated in FIG. 1.

As illustrated in FIG. 2, the member 54 is provided with an elongated keyslot 55 into which a guidepin 57 projects to prevent rotation of the member 54 which would result in misalignment of the cutting edges 68 and 70. The guidepin 57 is preferably formed as a socket head type screw which may have a prevailing torque type thread or thread insert so that the screw will be suitably retained in a set position in the housing portion 16 without forcibly engaging the bottom of the keyslot 55.

The members 54 and 72 may be formed of suitable hardenable tool steel or the like so that the cutting edges 68 and 70 may be hardened and ground to provide cutting edges which will withstand shearing forces exerted on stainless steel pin material and the like. The cutting edge 68 is formed by a substantially planar surface 69 parallel to the longitudinal axis of the member 54 and by a substantially transverse edge 71 provided with suitable rake to form an included angle for the cutting edge 68 in accordance with metal cutting practices. In like manner, the cutting edge 70 is formed by a planar surface 75 which is proportioned to be disposed closely adjacent to the surface 69. The cutting edge 70 also has a suitable included angle defined in part by a transverse surface 79.

The end portion 14 of the housing section 13 is provided with suitable tapped holes 90 and 91 spaced approximately 90° apart and extending transversely with respect to the longitudinal axis of the instrument 10. A handle member 92, including a threaded end portion 93, is removably disposed in the tapped hole 90 and may be alternately disposed in the tapped hole 91 whereby the handle may be conveniently located for enhanced manipulation of the instrument 10.

As illustrated in the drawing figures, the reduced diameter housing portion 14 includes a removable plug 94 whereby the chambers 19 and 23 may be filled with a suitable hydraulic fluid for actuating the piston 48 in response to movement of the piston 30 under the urging of the screw actuator 28.

The material strength requirements for intramedullary pins and the like are such that substantial cutting forces must be exerted in order to cut a pin in the range of 0.18 to 0.25 inches in diameter, which is a typical diameter range for intramedullary pins used in orthopedic surgery. Accordingly, a substantial axial force must be applied to the member 54 to provide a shearing action for severing a pin such as the pin 96, shown disposed in the bore 74 in FIG. 1. Moreover, it is important that, when cutting a pin that has already been inserted into the medullary cavity, minimal forces be applied to the pin lest further damage to the patient be incurred during the surgical procedure. Accordingly, the instrument 10 provides for exerting a substantial and adequate cutting force for such types of pins without imposing any substantial force on the pin itself after it has already been inserted into a bone. The combination of the screw actuator 28 and the hydraulic actuator comprising the pistons 30 and 48 disposed in the respective chambers 23 and 19 provides for a substantial axial force to be imposed on the member 54 to shear a pin along a transverse plane while only a nominal turning effort on the screw need be applied. Moreover, the provision of the laterally extending handle 92 provides for improved handling of the instrument 10, as well as counteracting the turning effort imposed on the screw actuator 28, so that a minimal lateral reaction force is imposed on the pin itself.

The operation of the instrument 10 to cut a pin such as the pin 96 is believed to be readily understandable from the foregoing description but a concise explanation will be provided herein. The normal position of the elements of the instrument 10 prior to cutting a pin would be substantially as shown in FIG. 2. The member 72 would be adjusted such that the cutting edge 70 would be in parallel alignment with the cutting edge 68. The member 72 would also be adjusted such that the transverse face 79 would be approximately aligned with an edge of the bore 74. The bore 74 is, of course, of sufficient diameter to allow a pin to be inserted past the cutting edge 70 when the member 72 is adjusted as described. When the instrument is in the relaxed position, the screw actuator 28 is retracted out of the housing section 14 far enough so that the spring 64 may push the piston 48 toward the wall 22 sufficiently that the cutting edge 68 does not extend into the bore 74. When it is desired to apply the instrument to cut a pin, the pin is inserted into the bore 74 and the screw actuator 28 is rotated to move the piston 30 downward, viewing FIG. 2. Fluid is displaced by the piston 30 from chamber 23 into the chamber 19 urging the piston 48 and member 54 toward the anvil 72. When a pin is severed by the shearing action of the cooperating cutting edges 68 and 70, the screw actuator 28 is rotated in the opposite direction and the spring 64 effects retraction of the pistons 48 and 30 to the respective positions shown in FIG. 2.

Since the fluid pressure in the chambers 19 and 23 is uniform throughout, a force exerted on the piston 30 is increased in proportion to the ratio of the transverse face areas of the pistons 48 and 30. Moreover, the axial force exerted by the screw actuator 28 is increased substantially over the actual force exerted on the head portion 32 or on a lever attached to the head portion. Of course, the force exerted to rotate the screw actuator 28 will depend on the radius of the lever arm connected to the head 32.

The mechanical advantage gained through rotation of the screw actuator 28 is also dependent on the pitch of the screw threads. It has been determined in accordance with the present invention that a screw actuator having nominal thread size of 0.625 inch diameter and 18 threads per inch UNF provides a suitable force multiplication in combination with pistons 30 and 48 having nominal diameters of one inch and two inches, respectively. Applying basic principles of mechanics for the ideal mechanical advantage of a screw actuator and multiplying that factor by the ratio of the diameters squared of the pistons 30 and 48, it can be seen that for the nominal dimensions given for the screw actuator and the pistons noted herein, that a force of 10 lbs., applied at a radius arm of two inches on the screw actuator 28, would produce an axial force on the cutting edge member 54 of 9150 lbs. neglecting friction in the screw and the pistons. This would be sufficient to shear a rod of 0.25 inches in diameter having a tensile strengh of 186,000 lbs. per square inch. Of course, the total torque applied to the screw actuator 28 may be varied considerably depending on the moment arm of the lever inserted in the bore 33 or another source of torsional effort such as a manual or power wrench applied to the head 32.

Those skilled in the art will appreciate that the compactness of the instrument 10 is a particularly attractive feature in regard to the requirements for handling the instrument in conjunction with surgical procedures. The reduced diameter section of the housing 16 permits placing the instrument closely adjacent to the portion of the bone from which the intramedullary pin extends so that the pin may be cut at the desired point. Moreover, the provision of the handle 92 aids in counteracting the torque exerted on the screw actuator 28 to minimize reaction forces exerted on the pin, particularly when the pin is already inserted into the medullary cavity.

The instrument 10 also includes the attractive features of replaceable cutting edges which may be easily replaced by interchanging the anvil member 72 and the cutting edge member 54 with replacement parts. Moreover, the member 54 and the anvil 72 may be easily removed from the instrument for sharpening the respective cutting edges 68 and 70. The instrument 10 may be constructed of conventional materials used for manual and power tools. The housing sections 13 and 15 as well as the handle member 92 may be made of aluminum, for example. The pistons 30 and 48 and the screw actuator 28 are preferably made of conventional engineering materials such as alloy or low carbon steel. Moreover, the instrument 10 can be completely sterilized using liquid or gas disinfectants as well as heat without adversely affecting the instrument components.

The instrument 10 has been adapted particularly for cutting intramedullary pins but the instrument could also be advantageously used for other pin cutting applications. Although a preferred embodiment of the present invention has been described herein in some detail, those skilled in the art will appreciate that various substitutions and modifications may be made to the present invention without departing from the scope and spirit of the appended claims.

What I claim is:

1. An instrument for cutting an elongated metal pin to a predetermined length by forcibly severing said pin, said instrument comprising:
   a housing including a first section forming a first cylindrical bore defining at least in part a pressure fluid chamber, and a portion supporting an anvil;
   a member disposed in said housing and movable relative to said anvil for engagement with a pin disposed against said anvil to forcibly sever said pin;
   a screw actuator mounted on said housing and enaged with a threaded part of said housing and operable to cause said member to move toward said anvil to sever said pin in response to rotation of said screw actuator;
   hydraulic force transmitting means interconnecting said screw actuator and said member including a first piston slidably disposed in said chamber and sealingly engaged with said bore, said first piston being connected to said member for moving said member toward said anvil in response to pressure fluid acting on said first piston, a second housing section including a second cylindrical bore of reduced diameter with respect to the diameter of said first bore, a second piston slidably disposed in said second bore and sealingly engaged with the wall of said second bore and delimiting said chamber, said second piston being interengaged with said screw actuator and responsive to axial movement of said screw actuator to displace pressure fluid in said chamber to move said first piston and said member toward said anvil for providing a substantial force acting on said member to sever said pin in response to a moderate turning effort exerted on said screw actuator, a handle connected to said second housing section and extending transversely with respect to the axis of rotation of said screw actuator for holding said instrument against rotation while said scrw actuator is being rotated to displace said second piston; and
   an elongated reduced diameter portion of said second housing including said second bore and further including at least two threaded holes for alternately receiving a threaded end portion of said handle.

2. A hand held instrument for cutting relatively hard metal intramedullary pins for use in orthopedic surgical procedures, said instrument comprising:
   a substantially cylindrical housing including a first housing section having a first bore defining at least in part a pressure fluid chamber, a first substantially uniform reduced diameter portion of said housing extending substantially coaxially from said first housing section and having a distal end, said first reduced diameter portion including a second bore coaxial with and opening into said first bore, a transverse hole in said first reduced diameter portion near said distal end and intersecting said second bore for receiving and journalling a pin to be cut;
   an anvil mounted at said distal end and adjacent to said transverse hole;
   a second substantially uniform reduced diameter portion of said housing extending directly from and substantially coaxial with said first housing section and substantially coaxial with said first reduced diameter portion and opposite said first reduced diameter portion, said second reduced diameter portion including a third bore opening into said chamber;
   a first piston disposed in said first bore;
   a rod member slidably disposed in said second bore and connected at one end to said first piston, said rod member including a transverse cutting edge on a distal end of said rod member opposite said one end and being movable toward said anvil in response to pressure fluid acting on said first piston to sever a pin disposed in said transverse hole and against said anvil;
   a second piston slidably disposed in said third bore and movable toward and away from said first piston to displace a quantity of pressure fluid in said chamber to urge said first piston and said rod member toward said anvil and to permit said first piston and said rod member to move away from said anvil, respectively;
   a screw actuator member threadedly engaged with cooperating threads formed on said second reduced diameter portion of said housing, and including a first end portion extending into said third bore;
   thrust bearing means in said third bore interposed between said first end portion of said screw actuator member and said second piston;
   a second end portion of said screw actuator member projecting from a distal end of said second reduced diameter portion of said housing, and means on said second end portion of said screw actuator member for rotating said screw actuator member to move said second piston toward said first piston; and
   handle means including said second reduced diameter portion of said housing and a handle member projecting from said second reduced diameter portion of said housing substantially normal to the axis of rotation of said screw actuator member to hold said instrument against rotation during rotation of said screw actuator member.

3. The instrument set forth in claim 2 wherein:
   said first reduced diameter portion includes means cooperable with said rod member for maintaining said cutting edge on said rod member parallel to a cooperating cutting edge on said anvil.

4. The instrument set forth in claim 3 wherein:
   said anvil comprises an integral threaded member having its cutting edge disposed on one end and having a threaded portion engaged with complementary threads formed on said distal end of said first reduced diameter portion whereby said anvil may be removably disposed on said first reduced diameter portion; and
   said anvil is secured to said first reduced diameter portion by a locknut threadedly engaged with said threaded portion of said anvil and engageable with said first reduced diameter portion for holding said anvil so that said cutting edge on said anvil may be secured in a predetermined position relative to said cutting edge on said rod member.

5. The instrument set forth in claim 4 including:
   a removable cap disposed on said first reduced diameter portion of said housing and covering said locknut.

6. The instrument set forth in claim 2 wherein:
   said rod member includes a threaded portion on said one end for removably connecting said rod member to said first piston.

7. The instrument set forth in claim 2 wherein:
   said second end portion of said screw actuator member includes a head having wrench engaging surfaces disposed thereon.

* * * * *

UNITED STATES PATENT AND TRADEMARK OFFICE
CERTIFICATE OF CORRECTION

PATENT NO. : 4,443,941
DATED : April 24, 1984
INVENTOR(S) : Jack L. McPhaul

It is certified that error appears in the above-identified patent and that said Letters Patent is hereby corrected as shown below:

Column 7, line 38, change "scrw" to --screw--.

Signed and Sealed this

Nineteenth Day of February 1985

[SEAL]

Attest:

DONALD J. QUIGG

Attesting Officer     Acting Commissioner of Patents and Trademarks